United States Patent [19]
Madsen

[11] Patent Number: 6,091,979
[45] Date of Patent: Jul. 18, 2000

[54] SUBDURAL ELECTRODE ARRAYS FOR MONITORING CORTICAL ELECTRICAL ACTIVITY

[75] Inventor: Joseph R. Madsen, Newton, Mass.

[73] Assignee: Children's Medical Center Corporation, Boston, Mass.

[21] Appl. No.: 09/111,328

[22] Filed: Jul. 7, 1998

[51] Int. Cl.$^7$ .................................................. A61B 5/042
[52] U.S. Cl. .......................... 600/377; 600/378; 600/393; 607/116; 607/117
[58] Field of Search ..................................... 600/372–378, 600/393, 544; 607/116, 117, 118, 119, 122, 129–141, 152, 11

[56] References Cited

U.S. PATENT DOCUMENTS

| | | | |
|---|---|---|---|
| 5,480,420 | 1/1996 | Hoegnelid et al. | 607/116 |
| 5,769,077 | 6/1998 | Lindegren | 607/122 |
| 5,902,236 | 5/1999 | Iversen | 600/377 |

FOREIGN PATENT DOCUMENTS

| | | |
|---|---|---|
| 0602859 | 6/1994 | European Pat. Off. . |
| 0783900 | 7/1997 | European Pat. Off. . |
| 95/19803 | 7/1995 | WIPO ................................... 600/374 |
| 9812243 | 3/1998 | WIPO . |

OTHER PUBLICATIONS

Guyton, A. "Human Physiology and Mechanisms of Disease" 5th ed. p. 275–276.

*Primary Examiner*—Linda C. M. Dvorak
*Assistant Examiner*—David Ruddy
*Attorney, Agent, or Firm*—Thomas J. Engellenner; Nutter, McClennen & Fish, LLP

[57] ABSTRACT

Electrodes arrays for monitoring in vivo electrical activity are disclosed. The arrays include a plurality of electrode contact pads in a predetermined spatial orientation held together by a structural matrix material that is preferably bioresorbable. The electrode pads are connected via lead wires to monitoring, analysis, and recording apparatus. The electrode arrays can be individually prepared, and configured (e.g., by irregular spacing between the electrode contact pads) to conform to the region undergoing analysis. Because the matrix material is substantially resorbed in the course of the protocol, the individual electrode cables will no long be attached to each other (or in the case of branching electrodes, the branches will no longer be fixed in position). In either instance, the electrode cables (or trunk and branches) can be removed without a second major operation.

21 Claims, 3 Drawing Sheets

SUBDURAL ELECTRODE ARRAYS FOR MONITORING CORTICAL ELECTRICAL ACTIVITY

BACKGROUND OF THE INVENTION

This invention relates generally to electrodes for monitoring cortical electrical activity and, in particular, electrode configurations and implantable devices for such electrical monitoring. The electrodes and implants are especially useful in monitoring cortical electrical activity to locate or define cortical epileptogenic foci.

Epilepsy affects approximately 2 million people in the United States and frequently begins during childhood. Although most cases of epilepsy are managed with medicines, some are best treated by locating and removing a specific lesion. These surgical procedures require detailed mapping to locate functional brain regions as well as the focus of epileptic activity. Epileptic foci may include mesial temporal sclerosis, focal cortical dysplasia, or other congenital neural development defects, or tumors. To evaluate these epilepsies, a common method has involved a highly invasive monitoring approach in which one or more multi-contact electrodes are implanted into the cortex, typically penetrating to the hippocampal depth. A problem with these deep penetrating electrodes is that the data obtained is limited to the local region in which they are placed. Furthermore, they require puncture of the brain surface for insertion. As a result of these limitations, the ability of such penetrating electrodes to study epilepsy outside their local region is sub-optimal.

In epilepsy outside of the temporal lobes, subdural electrode arrays are often employed and generally regarded as to be superior to intracortical penetrating electrodes. Subdural electrode arrays allow better localization of epileptogenic foci that are cortical in origin, and also allow mapping of brain tissue functions by the use of extra-operative stimulation. Due to the unpredictability of seizures, an extended period of time for recording of interictal and ictal activity is often needed to allow the investigator to map the epileptic focus prior to surgical resection. Long term monitoring of cortical electrical activity and in particular, long term monitoring via electrodes on the cortical surface, can yield a broader range of data regarding a seizure foci and the surrounding tissue. In addition, proper use of subdural electrodes causes less trauma and, hence, lower morbidity, in comparison to the use of intracortical penetrating electrodes with a similar capability of identifying epileptic foci.

Surgical removal of epileptogenic brain tissue is indicated for treatment of many epileptic seizure disorders. The optimal surgical outcome for the treatment of intractable seizures is only achieved following specific localization of the epileptic focus. This requires proper insertion and an understanding of the exact position of the subdural electrodes to obtain a proper interpretation of the recordings taken from the electrode contacts. Errors in the understanding of the position of the subdural electrodes can prevent accurate location of the epileptogenic foci. Great care must also be taken during insertion to avoid bending or folding the electrode, and to minimize any shift in the electrode position after insertion. This is particularly true with respect to separate arrays of subdural strip electrodes.

The prior art has attempted to overcome these limitations using two methods to prevent any bending or folding. The first includes greater structural support within the electrode body itself. The second is to create an electrode array by placing a plurality of electrodes on a rigid structure in a grid layout. These solutions however, have led to larger, more invasive, electrodes with the concomitant increase in difficulty and danger in inserting and removing them.

While grid electrode arrays exist in the prior art, they are typically rectangular electrode arrays with the contacts mounted on a rigid material. The contacts are usually monotonously separated. Thus, prior art grid electrode arrays are not designed to follow the specific contours of an individual or a particular area of the brain and, as a result, such rigid electrode grids can introduce errors in the location of the epileptogenic foci.

In addition, large grid structures, which may be as large as 8 cm×8 cm, require a large scale craniotomy for both insertion and again for removal of the rigid array with the inherent dangers associated with repeated resections of the cranium.

Thus, there exists a need for better subdural electrode structures. The electrode structure that can provide position stability to accurately determine the epileptogenic foci, and also allow for easy removal upon completion of the brain monitoring, would fulfill a long-felt need in the field.

SUMMARY OF THE INVENTION

Subdural electrodes arrays for determining epileptogenic foci are disclosed. These electrodes include a plurality of electrode contact pads in a predetermined spatial orientation held together by a structural material that is preferably bioresorbable. The electrode pads are connected via lead wires to monitoring, analysis, and recording apparatus. The electrode arrays can be individually prepared, and configured (e.g., by irregular spacing between the electrode contact pads) to conform to the cortical region undergoing analysis.

In one embodiment of the invention, a plurality of separate electrode cables are laid out in a predetermined spatial orientation, and are held in place by a bioresorbable material. A plurality of electrode contact pads and electrode lead wires electrically connected to each electrode contact pad are joined together to form each electrode cable. The bioresorbable material mechanically interconnects the cables and provides structural support as well. The degradation period of the bioresorbable material is pre-defined (e.g., by selection of a particular chemical composition) to coincide with the duration of the planned monitoring protocol, such that, after the bioresorbable material is reabsorbed, the electrode cables may then be removed individually (or as smaller components of the original array) without the need for a second large scale craniotomy.

In addition, each electrode cable in the electrode array can be constructed to have a substantially smooth cross-section and may be coated with a low surface friction material, or constructed with an outer cladding of a self-lubricating material such as polytetrafluoroethylene (PTFE) or other fluoropolymers. This allows the individual electrode cables to be easily withdrawn without snagging or otherwise damaging the cerebral cortical tissue.

In another aspect of the invention, the subdural electrode array can include a plurality of electrode pads which are electrically and/or mechanically connected with each other in a branching structure. The branching structure can again be held in place by a bioresorbable material structurally interconnecting the plurality of electrode pads.

In one embodiment, the branching structure can comprise a central trunk electrode cable interconnected with at least one branching electrode cable. The trunk electrode cable can be mechanically connected to one or more branching electrode cables and adapted to receive the branch electrode wires so that the entire electrode structure can be withdrawn together. This allows the lead wires from the branching electrode to pass through the trunk electrode cable to pass through the skull and to exit as a bundle. The branching electrodes can be retracted into a central sheath and removed together or simply withdrawn one at a time through the trunk.

Alternatively, the electrodes can be deployed like a set of independent fingers, initially held in predetermined positions but (upon degradation of the bioresorbable matrix material) withdrawn separately.

Whenever a branching structure is employed, it is preferable that the branches diverge at an acute angle relative to each other or relative to the trunk. For example, if the array is constructed like the veins of a leaf, each branching electrode should diverge from the trunk electrode at an angle between +90° and –90 relative to the trunk axis. This allows the branching electrodes to fold inward toward the trunk electrode and the entire array may then be easily withdrawn percutaneously.

In yet another aspect of the invention an implantable electrode device is shown having at least one sheet layer which assists in the placement or deployment of the array. In one preferred embodiment, two sheets of material are employed to "sandwich" the electrode array and prevent the electrode array from directly contacting the cortex and/or dura mater during implantation. Upon deployment of the array in the desired position relative to the cortical surface, the sheet or sheets can be removed as one of the final steps in the operation. Alternatively, one or more of the sheets can be left in place during monitoring and removed when the electrode array is dismantled, or the sheets can be fabricated from a biodegradable material that does not interfere with the electrical monitoring functions of the electrode pads.

The terms "bioresorbable" and "biodegradable" as used herein are intended to encompass the various known biocompatable materials that are resorbed or otherwise degraded over time within the in vivo environment. One skilled in the art will recognize that the rate of degradation of the material within the body can be controlled by adjusting the composition of the bioresorbable/biodegradable material. Example of suitable bioresorbable or biodegradable materials include poly-L-lactic acids, polylactic-coglycolic acid polymers, and polycaprolactones. Further suitable biodegradable or bioresorbable materials are described in U.S. Pat. Nos. 4,806,621; 5,399,665 and 5,654,381, each of which is incorporated herein by reference.

BRIEF DESCRIPTION OF THE DRAWINGS

The foregoing and other aspects of the present invention will be appreciated with reference to the detailed description of the invention which follows, which read in conjunction with the accompanying drawings wherein.

DETAILED DESCRIPTION

Figure 1:
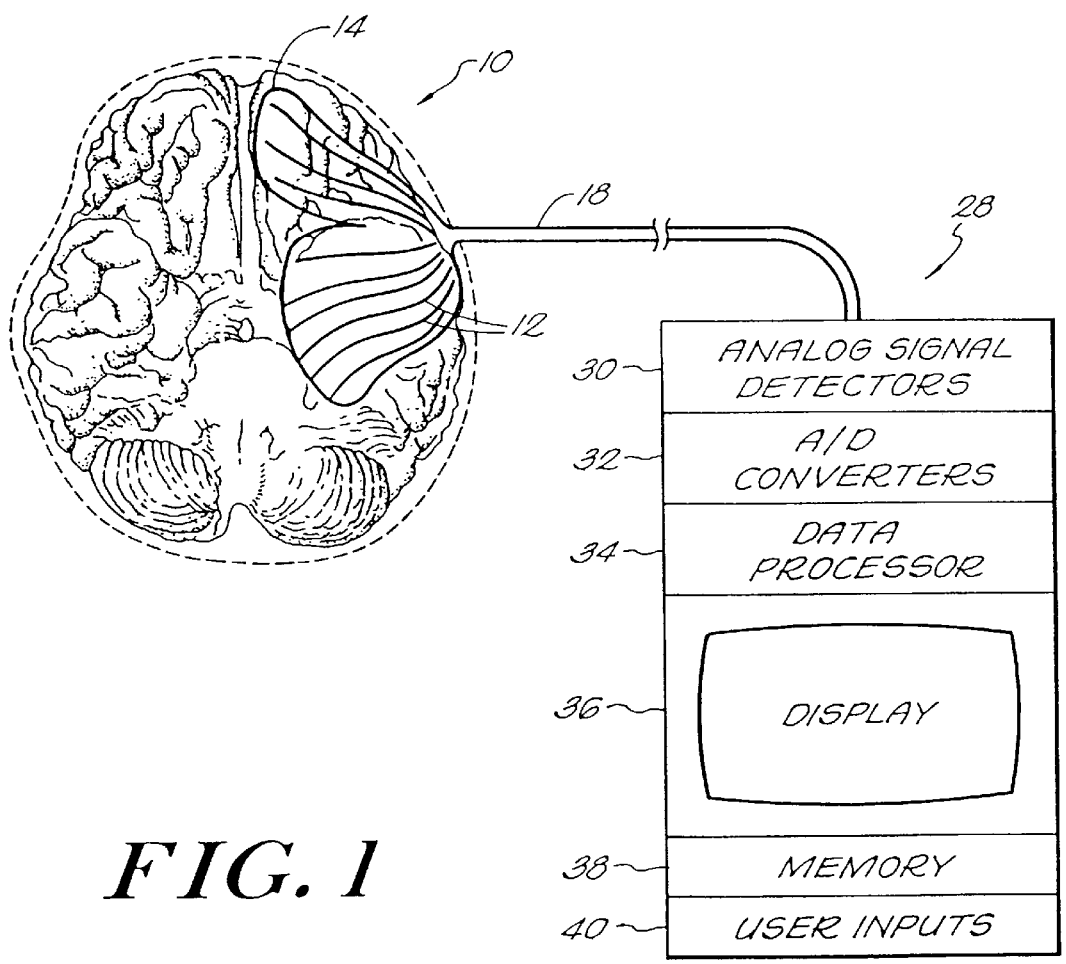
FIG. 1 is a schematic view of a subdural electrode array according to the present invention disposed within the subdural region of a brain and connected to an EEG recorder.

In FIG. 1 a subdural electrode array 10 according to the invention is shown, including electrode cables 12 that are structurally held in place by a matrix of bioresorbable material 14. The electrode lead wire 18 connects the pad 16 to a brain wave analyzer 28. The brain wave analyzer is typically an EEG device, commercially available from various sources, such as Bio-Logic Systems Corporation (Mundelein, Ill.) or Medtronic, Inc. (Minneapolis, Minn.). As shown the typical EEG device includes an analog processing component 30, one or more A/D converters 32, a data processor 34, a display 36, memory 38 and user inputs 40. Details on EEG apparatus and functions are well known in the art. See, for example, U.S. Pat. No. 4,949,725 issued to Raviv et al. on Aug. 21, 1990 and U.S. Reissue Pat. No. 34,015 issued to Duffy on Aug. 4, 1992, both of which are incorporated herein by reference.

Figure 2:
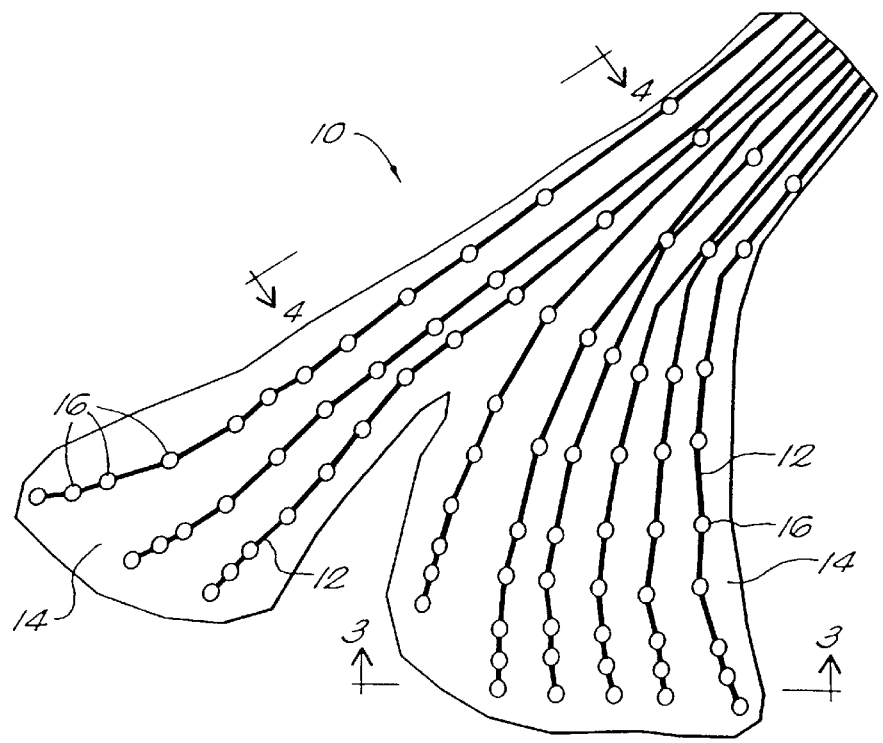
FIG. 2 is a top plan view of one embodiment of the subdural electrode array according to the present invention.

A more detailed view of the electrode array 10 is presented in FIG. 2. The electrode cables 12 each include at least one electrode contact pad 16 electrically coupled via an electrode lead wire to an EEG analyzer or similar instrumentation. As can be seen in FIG. 2, the spacing of the electrode contact pads 16 within the electrode cable 12 does not have to be monotonous. Instead, the spacing of the electrode contact pads 16 within the electrode cable 12 can be varied to optimize the data gathering performance of the electrode array. Additionally, the electrode cables 12 can be flexible and custom designed to conform to the contours of the brain in the area where the subdural electrode array 10 is inserted. This allows concentration of the electrode contact pads 16 in areas of higher interest, further optimizing the performance of the electrode array.

The bioresorbable material 14 is used to structurally interconnect the electrode cables 12 in their predetermined spatial orientation. The bioresorbable material 14, which may be a hemostatic substance, should be non-toxic, and have a reliable decomposition and absorption in the subdural space. The bioresorbable material can be any one of various known materials such as collagens, glycoaminoglycans, cellulose, oxidized celluloses, poly-L-lactic acid or polylactic-coglycolic acid polymers, polycaprolactones and the like. The bioresorbable material 14 does not have to be a solid sheet of material, gaps may be left between the electrode cables 12 (to reduce overall mass or hasten biodegradation). These gaps can reduce the amount of bioresorbable material needed for stable electrode deployment and can be used to establish the proper surface area to volume ratio necessary for the bioresorbable material 14 to decompose and be reabsorbed, within the proper time.

Figure 3:
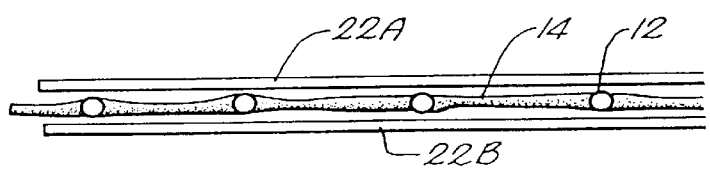
FIG. 3 is a cross-sectional view of the present invention taken along line 3—3 of FIG. 2 and including the flexible plastic sheets useful during insertion of the electrode array.
Figure 4:
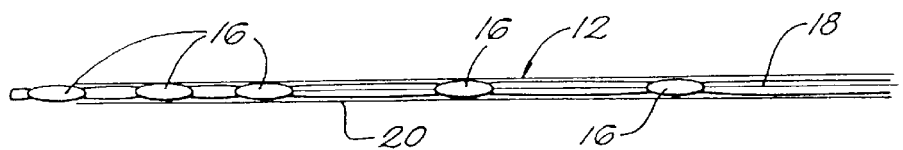
FIG. 4 is a cross sectional view of the present invention taken along line 4—4 of FIG. 2.

The electrode cables 12 can be formed by various construction techniques that are known in the art. In one embodiment, the electrode cable 12 may be made by sandwiching the electrode contact pads 16 and electrode lead wires 18 between two or more dielectric layers. In another embodiment, the electrode contact pads 16 and electrode lead wires 18 can also be placed within a hollow dielectric sheath having a substantially circular cross-section. In a preferred embodiment of the present invention, as shown in FIGS. 3 and 4, the electrode cable 12 has a substantially circular cross section that is smooth throughout its entire length, including where the electrode contact pads 16 are located. This permits atraumatic removal of the electrode cables 12 by preventing the electrode cable 12 from catching on and damaging cerebral cortical tissue. The term "electrode cable" as used herein is intended to encompass any carrier or conduit for one or more electrical conductors useful in electrically coupling one or more electrode pads or similar electrical signal pick-up devices to any detection, monitoring or analyzing apparatus.

In addition, a coating 20 (as shown in FIG. 4) can be applied to the electrode cables 12. The coating 20 should also be chosen so as to reduce and limit any tissue adhesion to the surface of the electrode 12 cable. For example, lubricating polymers such as hyaluronic acids, glycosaminoglycans and derivatives thereof, or Gliatek™ maybe used as the coating 20 to cover the electrode cable or electrode lead wires and provide adhesion limiting properties. In addition, the electrode cables may be constructed from a fluorocarbon polymer (or coated or sheathed by such a fluoropolymer) to provide a self-lubricating surface. Typical fluorocarbons can be polytetrafluoroethylene (PTFE) which is known by its trade name Teflon®. Other fluorocarbons that may be used include polytetrafluoroethylene (PTFE) fluorinated ethylene propylene (FEP), perfluroalkoxy (PFA) or tetraethylenepropylene (TFP).

During insertion the electrode cables 12 and bioresorbable matrix 14 can be held between two non-resorbable plastic sheets 22A, 22B (as shown in FIG. 3) to aid in the insertion process. To facilitate placement of the electrode array in the present invention, the bioresorbable matrix 14 and the plurality of electrode cables 12 contained therein, can be sandwiched between two protective flexible plastic sheets 22. The protective sheets 22A, 22B can be constructed, for example, of Silastic™ or silicone derivative membrane sheets and are used to place the array easily and accurately within the subdural space of the brain. More generally, the sheets can be any non-toxic, non-resorbable material that is designed to allow the subdural electrode 10 to facilitate placement or match the contours of the particular region of the brain which is to be evaluated. After insertion, the sheets and the subdural electrode 10 disposed therebetween can be irrigated with saline and one or both of the sheets 22A, 22B then withdrawn leaving the electrode array 10 properly placed and structurally intact with the electrode cables safely nestled by the matrix material 14. Alternatively, one or more of the sheets can also be constructed of a biodegradable material and left in situ to be resorbed by the body.

The suitability of the electrical contacts can then be tested, as is currently done with existing arrays. The individual cables will then be coupled to a brain wave analyzer or recording device 28 for long term monitoring. Depending on the geometry of the subdural electrode array, individual access sites can be resected for the electrode cables, or a plastic conduit can be implanted through a larger scalp incision to guide a plurality of the cables through the cranium from the subdural space to the electrical signal analyzer.

Figure 5:
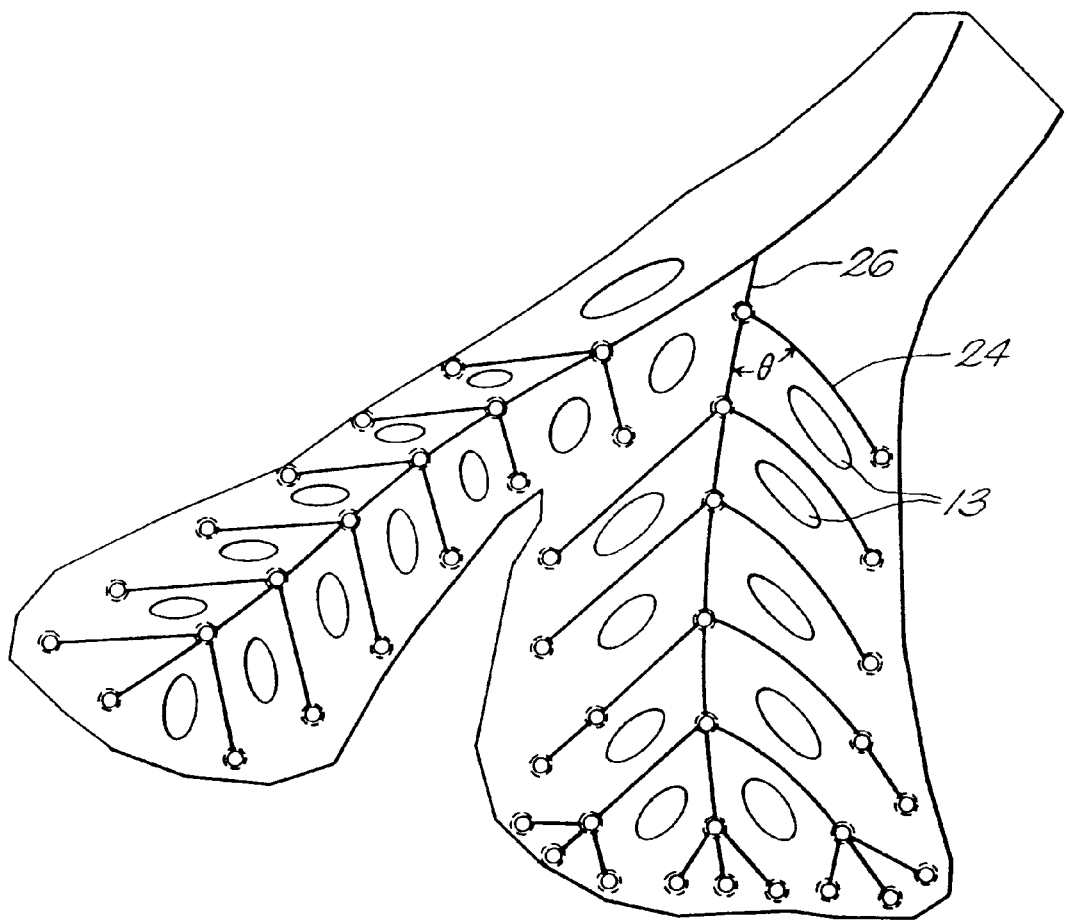
FIG. 5 is a top view of another embodiment of the present invention showing a branching electrode array structure.

FIG. 5 shows another embodiment of the subdural electrode 24 that utilizes a branching structure of the electrode cables 12. The branching structure comprises a trunk electrode 26 from which branch electrode cables 28 extend outward therefrom. The branch electrode cables 28 are attached to, and communicate with, the trunk electrode cable 26, such that the electrode lead wires from the branch electrode cables 28 cables are passed through the trunk electrode cable 26 and out from the proximal end of the trunk electrode cables 26. The branch electrode cables 28 are attached to the trunk electrode 26 at an acute angle designated by symbol θ which is preferably between −90° and +90° as indicated in the figures.

The branch electrodes 28 should be within this angular range to ensure that the branches fold away from the direction in which the electrodes are removed. As the trunk electrode 26 is removed the branch electrodes 28 collapses onto the trunk electrode 26 for easier removal. The branching structure allows the cables to be removed without dangerously bunching up or crossing over and damaging cerebral cortical tissue. This allows an electrode array structure which was capable of recording electrical signals over sizable portion of the brain to be removed safely, easily, and percutaneously.

It is obvious that many geometries of branching maybe used depending upon the area of the brain in which the electrical activity is to be measured. The spacing of the electrode contact pads 16 within the electrode cables 12 and the placement and length of the branching electrode 28 should be such that the electrode contact pads are concentrated the points of greatest interest, such as the mesial temporal structures as described above. In addition, the branch electrode cables 28 may themselves be trunk electrodes and that further levels of branching structures can be attached to the branch electrode cables 28 in order to cover a greater surface area of the brain. Preferably these further branching structures are also oriented to diverge from the trunk or each other at acute angles, in order to facilitate the collapsing of the branching structure during removal of the electrode cables percutaneously, and to prevent damage to the cerebral cortical tissue.

In use, the electrode arrays of the present invention are deployed in the subdural region following an cranial resection. EEG monitoring can begin either on the day of surgery or the first postoperative day. The monitoring is preferably done in conjunction with electronic recording. For example, the patients' EEGs can be recorded with a Telefactor 64-channel EEG multiplexed instrument that combines video and audio recordings onto videotape. Typically, the recording duration will range from about 3 to about 23 days. In one protocol, the patient is initially monitored without changing the dosages of his or her antiepileptic drugs. If no ictal events can be adequately recorded, medication is tapered after 48 hours. After obtaining sufficient ictal (usually more than 3 typical events) and interictal recordings, cortical stimulations and mapping of somatosensory areas by evoked potentials can be performed. (Patients should have their antiepileptic drugs reintroduced prior to mapping to reduce the risk of precipitating seizures with the cortical stimulations.)

Upon completion of mapping and recording, the electrodes can be removed. Because the matrix material is substantially resorbed in the course of the protocol, the individual electrode cables will no longer be attached to each other (or in the case of branching electrodes, the branches will no longer be fixed in position). Thus, in either instance, the electrode cables (or trunk and branches) can be removed without a second major reopening of the cranium.

It should also be noted that the invention can also be applied to monitoring the electrical activity of other body structures such as, for example, the heart. To map electrically activity on the outer surfaces of the heart (or particular segments of the heart) the present invention can be deployed with the same beneficial effects: ensuring the maintenance of electrode spacing during monitoring and/or facilitating less traumatic electrode extraction.

While preferred embodiments of the present invention have been described, it should be appreciated that many modifications and variations thereto are possible all of which would fall within the scope of the claims which follow.

What is claimed is:

1. An electrode array for cranial implantation comprising:
a plurality of electrode cables for detection of electrical activity in a patient's body following implantation, and
a bioresorbable material connected to the plurality of electrode cables, for maintaining the cables in an initial predetermined spatial relationship and having a degradation period that corresponds with the period of intended use of the array to facilitate removal of the array.

2. An electrode array as in claim 1, wherein the electrode cables comprise at least one electrode contact pad disposed within each cable, an electrode lead wire disposed within the electrode cable, and the electrode lead wire being in electrical communication with the electrode contact pad.

3. A electrode array as in claim 2 wherein the electrode contact pad is dimensioned such that the cross sectional area of the electrode cable is substantially smooth.

4. A electrode array as in claim 1 wherein the electrode cable is coated with a low friction surface material.

5. A electrode array as in claim 4 wherein the low friction coating material is a lubricating polymer selected from the group of hyaluronic acids, glycosaminoglycans and derivatives thereof.

6. A electrode array as in claim 1 wherein the electrode cable is comprised of a fluorocarbon.

7. A electrode as in claim 6 wherein the fluorocarbon is selected from the group consisting of polytetrafluoroethylene (PTFE) fluorinated ethylene propylene (FEP), perfluroalkoxy (PFA) and tetraethylenepropylene (TFP).

8. The electrode array as in claim 7 wherein the fluorocarbon is PTFE.

9. A electrode array as in claim 1 wherein the bioresorbable material is a hemostatic substance.

10. A electrode array as in claim 1 wherein the bioresorbable material is selected from the group of collagen, oxidized cellulose, poly-L-lactic acid, polylactic-coglycolic acid polymers, polycaprolactone and derivatives and combinations thereof.

11. A electrode array for cranial implantation comprising:
at least one electrode cable having a branching structure for detection of electrical activity in a patient's body following implantation, and
a bioresorbable material connected to the branching structure of the electrode cable, for maintaining the cables in an initial predetermined spatial relationship and having a degradation period that corresponds with the period of intended use of the array to facilitate removal of the array,
whereby after the bioresorbable material is reabsorbed, said at least one electrode cable may be withdrawn percutaneously.

12. A electrode array as in claim 11 wherein the branching structure comprises:
a trunk electrode cable having at least one electrode contact pad disposed within the trunk electrode cable and an electrode lead wire disposed within the trunk electrode cable and in electrical communication with the electrode contact pad,
at least one branch electrode cable, the branch electrode having at least one electrode pad disposed within the branch electrode cable and an electrode lead wire disposed within the first branch electrode cable in electrical communication with the electrode pad,
the branch electrode cable being affixed to the trunk electrode cable, and communications therewith, such that the branch electrode cable makes an angle with the trunk electrode of between 90° and −90°.

13. A electrode array as in claim 12 wherein the branch electrode cable is coated with a low friction surface material.

14. A electrode array as in claim 13 wherein the low friction coating material is a lubricating polymer selected from the group of hyaluronic acids, glycosaminoglycans and derivatives thereof.

15. The electrode array as in claim 11 wherein the electrode cable is comprised of a fluorocarbon.

16. The electrode array as in claim 15 wherein the fluorocarbon is PTFE.

17. The electrode array as in claim 16 wherein the fluorocarbon is FEP.

18. The electrode array as in claim 16 wherein the fluorocarbon is PFA.

19. The electrode array as in claim 16 wherein the fluorocarbon is TFP.

20. A electrode array as in claim 11 wherein the bioresorbable material is a hemostatic substance.

21. A electrode array as in claim 11 wherein the bioresorbable material is selected from the group of collagen, oxidized cellulose, poly-L-lactic acid, polylactic-coglycolic acid polymers, polycaprolactone and derivatives and combinations thereof.

* * * * *

UNITED STATES PATENT AND TRADEMARK OFFICE
CERTIFICATE OF CORRECTION

PATENT NO. : 6,091,979
DATED : July 18, 2000
INVENTOR(S) : Joseph R. Madsen It is certified that error appears in the above-identified patent and that said Letters Patent is hereby corrected as shown below:

Col. 4, line 35 and 36:

<u>Reads</u>: "material 14, which may be a hemostatic substance,"

<u>Should read</u>: --material 14 should be non-toxic, and--

Signed and Sealed this

Fifteenth Day of May, 2001

Attest:

NICHOLAS P. GODICI

Attesting Officer     Acting Director of the United States Patent and Trademark Office

UNITED STATES PATENT AND TRADEMARK OFFICE
CERTIFICATE OF CORRECTION

PATENT NO.    : 6,091,979
DATED         : July 18, 2000
INVENTOR(S)   : Joseph R. Madsen It is certified that error appears in the above-identified patent and that said Letters Patent is hereby corrected as shown below:

<u>Column 4,</u>
Lines 35-36, "material 14, which may be a hemostatic substance," should read
-- material 14 should be non-toxic, and --

Signed and Sealed this

Fifth Day of October, 2004

JON W. DUDAS
*Director of the United States Patent and Trademark Office*